United States Patent [19]

Schmid

[11] 4,436,089
[45] Mar. 13, 1984

[54] PRESSURE DRESSING WITH CUSHION

[76] Inventor: Eduard Schmid, Böheimstrasse 37, D7000 Stuttgart 1, Fed. Rep. of Germany

[21] Appl. No.: 321,168
[22] PCT Filed: Mar. 11, 1980
[86] PCT No.: PCT/DE80/00028
§ 371 Date: Nov. 9, 1981
§ 102(e) Date: Nov. 9, 1981
[87] PCT Pub. No.: WO81/02517
PCT Pub. Date: Sep. 17, 1981

[51] Int. Cl.³ .............................................. A61F 13/00
[52] U.S. Cl. ..................................................... 128/155
[58] Field of Search ................ 128/95, 96, 112, 117, 128/118, 157, 155, 156, 163, 165, DIG. 20

[56] References Cited

U.S. PATENT DOCUMENTS

| 397,545 | 2/1889 | Greeno | 128/118 |
| 404,307 | 5/1889 | Rorick | 128/118 |
| 413,152 | 10/1889 | Streeter et al. | 128/118 |
| 449,473 | 3/1891 | Garcia | 128/118 |
| 571,969 | 11/1896 | Fredin | 128/118 |
| 1,526,795 | 3/1923 | Knapp | 128/118 |
| 1,925,615 | 9/1933 | Stuart | 128/112 |
| 2,070,727 | 2/1937 | Hamann | 128/117 |
| 2,367,690 | 7/1943 | Purdy | 128/154 |
| 3,874,387 | 4/1975 | Barbieri | 128/155 |
| 4,202,331 | 5/1980 | Yale | 128/155 |
| 4,257,412 | 3/1981 | Guttentag | 128/112 |
| 4,303,063 | 12/1981 | Stahl | 128/163 |

FOREIGN PATENT DOCUMENTS

| 1491207 | 4/1969 | Fed. Rep. of Germany . |
| 1915636 | 10/1970 | Fed. Rep. of Germany . |
| 627900 | 10/1927 | France | 128/118 |

Primary Examiner—Richard J. Apley
Assistant Examiner—Harry J. Macey
Attorney, Agent, or Firm—Burmeister, York, Palmatier, Hamby & Jones

[57] ABSTRACT

A pressure dressing provided with a cushion for tightly holding an element of grafted skin, wherein the portion opposite the portion in contact with the body (5) has a rigid plate (4).

6 Claims, 4 Drawing Figures

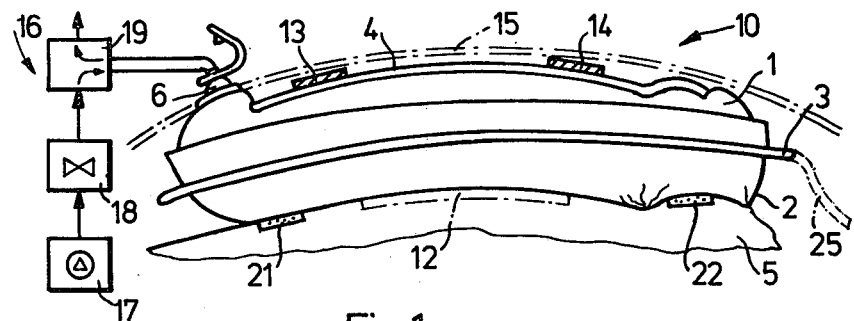
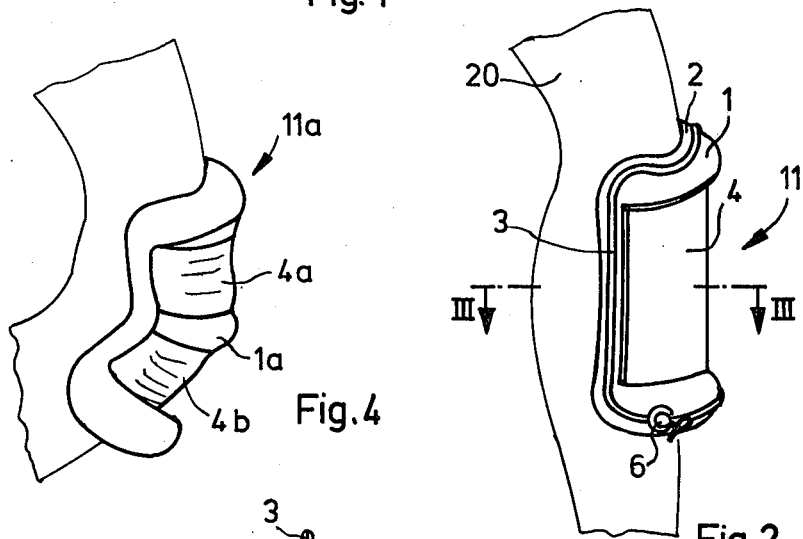
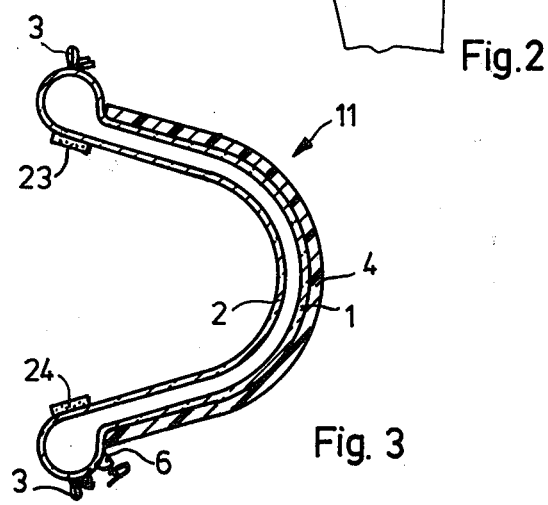
Fig. 1
Fig. 4
Fig. 2
Fig. 3

PRESSURE DRESSING WITH CUSHION

FIELD OF THE INVENTION

The present invention relates to a cushion containing bandage or dressing for holding skin grafts tightly in position.

BACKGROUND OF THE INVENTION

In the surgical grafting of skin sections, especially when a full-thickness skin transplantation is performed, it is of critical importance that uniform pressure be applied to the graaft over the entire area thereof to press the transplanted skin firmly against the respective surface area of the human body. Such evenly applied pressure must be maintained from six to eight days, with slight individual variations being permissible. It is known to use for this purpose a pressure dressing which includes a cushion of a size larger than the section of the grafted skin so that the graft is evenly pressed over its entire surface area against the lesion. (Ferris Smith: Plastic and Reconstruction Surgery, W. B. Saunders Co., 1950, pages 26 and 27.)

However, even with the most meticulous care it is not always possible to protect the surface area of the cushion in contact with the grafted skin from the effects of the pressure exerted by the bandage, resulting in the formation of folds in the cushion, especially when the skin is grafted onto a strongly curved body part and the transplanted skin section is large. Such folds in the cushion tend to cause corresponding impressions or similar folds in the transplanted skin which remain visible even after complete healing.

SUMMARY OF THE INVENTION

It is the object of the present invention to overcome the afore-mentioned disadvantage and to provide a pressure dressing for use with skin grafts. This is accomplished according to the invention in that the cushion is provided with a rigid plate on the side opposite the area of contact with the body.

The beneficial effect of the invention is that the pressure exerted by the bandage as applied is distributed evenly by way of the plate over the entire cushion. In addition, the cushion, which is usually filled with air or water, is prevented by the rigid plate from becoming indented when the first turn of the pressure bandage is applied over the cushion, whereby portions of the surface of the air filled cushion applied to the grafted skin may be slightly displaced relatively to the body surface, causing the formation of folds in the cushion, even if the sheet or foil of which the cushion is made, and which is in contact with the body surface, is resilient.

The size of the plate should be so selected that the plate is capable of performing the functions of pressure distribution and prevention of a notching or cave-in of the cushion. In one embodiment of the invention, the plate is at least approximately as large as the skin graft, so that the formation of folds in the area of the skin graft can be prevented with a high degree of probability.

According to another embodiment of the invention, the plate is shaped to conform to the contours of the surface of the body. For example, if the pressure dressing is to be applied to an extremity, the plate may be approximately dish-shaped. The shape of a particular part of the human body may also be accommodated by using a plurality of plates put together to arrive at the desired configuration. For example, the entire periphery of a leg section may be covered by an assembly of plates placed closely adjacent each other. In this instance, the cushion is disposed between such assembly of plates and the surface of the leg. This embodiment of the invention is well suited, for example, for use in the surgical treatment of elephantiasis. While an inflatable air splint has become known from a publication by G. Schwager in Plastic and Reconstructive Surgery, Vol. 37, No. 4, April 1976, p. 523, apparently consisting of a transparent air cushion encasing an extremity and pulled over the dressing and then inflated, the problem with which the present invention is concerned, namely, folds forming on the side of the cushion which is in contact with the body being transferred as deformations onto the grafted skin, is not even recognized in the first place in this prior art proposal, because the inflatable cushion is placed over the dressing or bandage, whereas the formation of skin folds depends on the degree of skill with which the dressing was applied.

In another embodiment of the invention, the plate is made of a transparent material. This enables the person applying the pressure dressing to visually inspect through the plate the side of the cushion in contact with the body surface as the pressure dressing is being applied, and to observe whether any folds are forming. In a modification of this embodiment, the side of the cushion in contact with the body is made of a transparent material, for example, a transparent foil or sheet, so that it is possible to visually examine the grafted skin section without the necessity of having to remove the dressing, provided, that a corresponding window has been cut out from the portion of the dressing arranged above the cushion.

BRIEF DESCRIPTION OF THE DRAWINGS

Illustrative embodiments of the invention are shown in the accompanying drawings, in which:

FIG. 1 is a side view of a cushion according to one embodiment of the invention;

FIG. 2 is a perspective view of another embodiment, including a strongly curved plate;

FIG. 3 is a sectional view of the embodiment of FIG. 2; and

FIG. 4 is a perspective view of another embodiment, similar to that of FIG. 2.

DETAILED DESCRIPTION OF ILLUSTRATIVE EMBODIMENTS

Referring to the drawings, the cushions 10 and 11 according to the illustrated embodiments comprise two foil cuttings or sheets 1 and 2 of latex rubber or a suitable, preferably resilient, plastic material, joined at their edges by a seam 3 so as to be impervious to air. The foil or sheet 1 on the side of the cushions 10, 11 facing away from the body surface area 5 to be dressed is provided with a rigid plate 4 welded or adhesively attached to the sheet 1, or fixedly held in position in some other way. The plate 4 has a shape which conforms to the surface area of the body part 5 onto which a skin section 12 is to be transplanted. The rigidity and size of the plastic plate 4 enable the plate 4 to uniformly distribute the pressure exerted by a pressure dressing 13, 14, 15 over the entire surface area of the cushion 10, 11 and thereby prevent the foil or sheet 2 on the underside of the cusion 10, 11 from forming folds. Preferably, the plate 4 is of a size equal to or larger than the grafted skin section 12.

The plate 4 consists of a transparent material and the foils 1 and 2 are likewise transparent. Providing that the pressure dressing 13, 14, 15 has a window at the corresponding place, it is possible to view the skin graft 12 through such window, the transparent plate 4 and the transparent foils 1 and 2.

In the proximity of the edge of the cushion 10, 11, the foil 1 has welded therein a valve 6 to enable the cushion 10, 11 to be filled with water or air. The valve 6 is so constructed that devices 16 for producing 17, maintaining 18 and/or controlling 19 of the pressure inside the cushion 10, 11 may be readily connected thereto.

FIGS. 2 and 3 illustrate an embodiment of the inventive cushion 11 which is adapted to match the configuration of a shinbone 20. For the sake of clarity, the pressure dressing and the pressure devices are omitted in FIGS. 2 and 3. The plate 4 is strongly curved to conform to the general shape of the tibia, as it is particularly clear from FIG. 3.

The cushion 10, 11 may be attached to the body by means of a bandage or an elastic hose or in some other manner as, for instance, an adhesive 21, 22, 23, 24. The two foils 1 and 2 may be of different size; for instance, the sheet 2 in contact with the skin may extend beyond the seam 3 so as to assist in the fastening of the cushion, as indicated at 25 in FIG. 1. Furthermore, as shown in FIG. 4, a plurality of curved and/or plane plates 4a, 4b may be secured on the cushion 11a to form an assembly which is flexible or articulate due to the resilient nature of the foil 1a of which the cushion 11a is made.

The plate 4 may consist of a thermoplastic material which can be heated and molded to fit the particular body portion to which it is to be applied. This can be done prior to applying the dressing, or before or after the plate is attached to the cushion.

I claim:

1. A skin graft pressure dressing for pressing a skin graft against a body member,
   said pressure dressing comprising in combination:
   a fluid-containing cushion for engaging and exerting pressure against the entire skin graft and the surrounding normal skin on the body member,
   said cushion having thin flexible walls enclosing a space for receiving a fluid material,
   said walls being made of a thin flexible resilient foil material,
   a rigid pressure plate engaging said cushion on the side thereof opposite from the skin graft for pressing said cushion against the skin graft and the surrounding normal skin,
   said plate being made of a transparent material,
   the foil material between said plate and the skin graft also being transparent to render the skin graft clearly visible for inspection through said plate and said cushion,
   means for securing said plate to the body member while exerting pressure upon said plate to press said plate against said cushion so that said cushion will exert pressure against the skin graft,
   and means for producing, maintaining and controlling the pressure of the fluid material within said cushion.

2. A skin graft pressure dressing according to claim 1, in which said plate is made of transparent thermoplastic material which is moldable in shape with the aid of heat.

3. A skin graft pressure dressing according to either claim 1 or 2, in which said plate has a shape conforming generally to the shape of the body member on which the skin graft is to be mounted.

4. A skin graft pressure dressing according to claim 1, 2 or 3, in which said plate is fixedly secured to said cushion.

5. A skin graft pressure dressing according to claim 1, 2 or 3, in which said plate is one of a plurality of plates secured to said cushion.

6. A skin graft pressure dressing according to claim 1, 2, 3, 4 or 5, in which said fluid material in said cushion is compressed air, the pressure of which is produced, maintained and controlled by said last mentioned means.

* * * * *